(12) United States Patent
Danks et al.

(10) Patent No.: US 7,763,433 B2
(45) Date of Patent: Jul. 27, 2010

(54) ANALYTE DETECTION SYSTEM

(75) Inventors: Christopher Danks, Sand Hutton (GB); Jonathan Richard Flint, Sand Hutton (GB)

(73) Assignee: Forsite Diagnostics Limited, Leeds (GB)

( * ) Notice: Subject to any disclaimer, the term of this patent is extended or adjusted under 35 U.S.C. 154(b) by 457 days.

(21) Appl. No.: 11/571,481

(22) PCT Filed: Jun. 30, 2005

(86) PCT No.: PCT/GB2005/002564

§ 371 (c)(1),
(2), (4) Date: Feb. 15, 2007

(87) PCT Pub. No.: WO2006/003394

PCT Pub. Date: Jan. 12, 2006

(65) Prior Publication Data

US 2008/0289068 A1 Nov. 20, 2008

(30) Foreign Application Priority Data

Jul. 1, 2004 (GB) .............................. 0414725.2
Jul. 1, 2004 (GB) .............................. 0414726.0

(51) Int. Cl.
*G01N 33/53* (2006.01)
(52) U.S. Cl. ................... 435/7.1; 435/7.92; 435/7.94; 435/4; 435/960; 435/969; 436/514; 436/518
(58) Field of Classification Search ............. 436/518, 436/514; 435/7.1, 7.92, 7.94
See application file for complete search history.

(56) References Cited

U.S. PATENT DOCUMENTS

| | | | | |
|---|---|---|---|---|
| 5,602,040 A | * | 2/1997 | May et al. | 436/514 |
| 5,766,961 A | * | 6/1998 | Pawlak et al. | 436/510 |
| 6,001,658 A | | 12/1999 | Fredrickson | |
| 6,096,563 A | * | 8/2000 | Hajizadeh et al. | 436/523 |
| 6,509,196 B1 | | 1/2003 | Brooks et al. | |

(Continued)

FOREIGN PATENT DOCUMENTS

EP 0 282 192 A1 9/1988

(Continued)

OTHER PUBLICATIONS

EPO Search Report for GB 0414726.0, dated Sep. 14, 2004, 2 pgs.

(Continued)

*Primary Examiner*—Bao-Thuy L Nguyen

(57) ABSTRACT

A method for the determination of a target analyte in a sample, said method comprising: a) applying a liquid sample suspected of containing said target analyte to a solid support capable of allowing lateral flow of liquid there through, which support has diffusibly arranged thereon, (i) either (a) a labeled binding partner for said analyte or (b) a labeled analogue of said analyte, and (ii) a labeled control reagent; b) allowing the sample, labeled binding partner for said analyte or a labeled analogue of said analyte and labeled control reagent to flow through a detection zone on said solid support; c) allowing the sample, labeled binding partner for said analyte or a labeled analogue of said analyte and labeled control reagent to flow through a control zone; and d) detecting the labeled density in the detection zone and the label density in the control zone and comparing these densities.

23 Claims, 7 Drawing Sheets

U.S. PATENT DOCUMENTS

| | | |
|---|---|---|
| 7,097,983 B2 | 8/2006 | Markovsky et al. |
| 7,132,078 B2 | 11/2006 | Rawson et al. |
| 2003/0119203 A1 | 6/2003 | Wei et al. |
| 2003/0162236 A1 | 8/2003 | Harris et al. |
| 2004/0018637 A1 | 1/2004 | Politto et al. |

FOREIGN PATENT DOCUMENTS

| | | |
|---|---|---|
| EP | 0 291 194 A1 | 11/1988 |
| EP | 0 462 376 A2 | 12/1991 |
| EP | 1 043 336 A2 | 10/2000 |
| GB | 2 300 914 A | 11/1996 |
| WO | WO 97/06439 A1 | 2/1997 |
| WO | WO 97/09620 A1 | 3/1997 |
| WO | WO 00/31538 A1 | 6/2000 |
| WO | WO 00/42434 A1 | 7/2000 |
| WO | WO 01/42787 A3 | 6/2001 |
| WO | WO 02/065128 A2 | 8/2002 |
| WO | WO 03/060134 A1 | 7/2003 |
| WO | WO 2006/003394 A1 | 1/2006 |

OTHER PUBLICATIONS

EPO Search Report for GB 0414725.2, dated Oct. 6, 2004, 1 pg.
International Search Report for PCT/GB2005/002564, dated Oct. 6, 2005, 2 pgs.
Lawrence, J.F. et al. "Use of immunoaffinity chromatography as a simplified cleanup technique for the liquid chromatographic determination of phenylurea herbicides in plant material", *J. Chrom.* (1996), vol. 732, pp. 277-281.
Lawrence, J.F. et al., "Evaluation of immunoaffinity chromatography as a replacement for organic solvent clean-up of plant extracts for the determination of triazine herbicides by liquid chromatography", *J Chrom* (1996), vol. 752, pp. 147-154.
Lee, J.K. et al., "Development of an Enzyme-Linked Immunosorbent Assay for the Detection of the Organophosphorus Insecticide Acephate", *J. Agric. Food Chem* (2003), vol. 51, pp. 3695-3703.

\* cited by examiner

ANALYTE DETECTION SYSTEM

The present application relates to a method for conducting an assay for a target analyte present in a sample, in particular a semi-quantitative assay, as well as to assay devices and kits for use in the method. The method and apparatus is particularly useful in the detection of analytes such as agrochemicals, hormones, pests, toxins or drugs.

The detection of analytes such as proteins on a variety of solid supports is well known in the art. Many such tests are in the form of "dipstick" assays which rely on lateral flow of liquid sample containing the analyte along a membrane, where they encounter labels, labelled binding partners and/or immobilised binding partners, in a sequence whereby a detectable visible signal is developed on the membrane. Such methods are advantageous in that they provide rapid results, and may be used by unskilled operators in almost any location.

For instance, they may be utilised in agriculture to detect particular pests or pathogens on crop plants, such as fungal antigens or viral infections.

In certain situations a simple positive or negative result, indicative of the presence or absence of analyte, is all that is necessary. For example such assays are commonly used in pregnancy tests, and the mere presence of a specific hormone, such as HCG, is indicative that that subject is pregnant.

However, in certain situations, a more quantitative approach may be required, in order to obtain at least some indication of the level at which a particular analyte may be present in a sample. This may find particular use in for example food testing where regulatory authorities may permit a particular moiety, such as a contaminant or the like, may be present in a food stuff, but only up to a certain level. Particular examples of contaminants include pesticide residues, which may be found for example on fruit and vegetable products, or drugs or other substances administered to animals during their lives, traces of which may remain in animal products such as meat, fish or milk.

The presence of higher levels of the moiety would mean that that the foodstuff was unacceptable for the intended purpose. Therefore the amount of analyte must be quantified, at least on a semi-quantitative level, to determine whether such a level is reached.

Alternatively in animal husbandry, levels of particular reagents such as hormones in a body fluid may need to be determined. Requirements for determining at least semi-quantitatively, the levels of hormones associated with fertility arise widely in animal husbandry, for example in stud and dairy farms. For example, all milk will naturally contain some progesterone hormone, but the level of this hormone will vary depending upon the fertility cycles of the cow. By monitoring these levels, the optimum times for insemination of the cow may be determined.

Similarly the levels of stress hormones such as cortisol may be measured in, for instance saliva samples, from a variety of farm animals such as pigs, sheep and cows, for welfare purposes. For instance, it is known that animals may suffer stress during transport if they are overcrowded or lacking in food or water, or have been travelling for extended periods of time. A rapid test to determine the stress levels amongst animals undergoing transport or in other stressful situations will assist in ensuring their welfare.

In agriculture also, the levels of a particular agrochemical present in any particular situation would be helpful in determining for instance whether further treatment is required.

A rapid semi-quantitative method, in which the detection of levels above a certain threshold level is measured, would be desirable in these instances.

Some semi-quantitative methods which utilise the convenient lateral flow format are known. For example WO 00/42434 and GB 2300914 disclose assay devices where more than one detection zone is provided along a test stick, and the amount of target analyte can be related to the number of zones which show a positive result after the sample has been run.

EP0462376 discloses an assay using a dual readout system having a capture site to which a capture reagent, which competes with the analyte for binding to the labelled conjugate, is attached and a conjugate recovery site to which is attached a conjugate recovery agent. The immobilization of conjugate in this site is then related to the amount of analyte in the test sample where a decrease in detectable conjugate at the capture site and a corresponding increase in detectable conjugate at the conjugate recovery site indicates an increasing amount of analyte in the sample.

WO97/09620 describes quantitative and semi-quantitative assays, where the signal generated by the target analyte at a detection zone is compared to a signal generated at a range of calibration zones, to determine whether the quantity of analyte in a sample is above or below the levels equivalent to those that are set by the calibration zones. Standard curve data may be used to calculate the amount of analyte in a sample.

In order to accurately quantitate an analyte in a sample, it is generally necessary to compare with a wide range of standards, which should be run on each occasion. This means that the assay devices are complex and interpretation of results may require input from a skilled operator.

The applicants have devised a simple assay, which gives rapid results easily.

According to a first aspect of the present invention there is provided a method for the determination of a target analyte in a sample, said method comprising:

a) applying a liquid sample suspected of containing said target analyte to a solid support capable of allowing lateral flow of liquid therethrough, which support has diffusibly arranged thereon, (i) either (a) a labelled binding partner for said analyte or (b) a labelled analogue of said analyte, and (ii) a labelled control reagent;

b) allowing the sample, labelled binding partner for said analyte or a labelled analogue of said analyte and labelled control reagent to flow through a detection zone on said solid support, wherein in the case of (i)(a) above, a predetermined amount of an analogue of the target analyte is immobilised, or, in the case of (i)(b) above a predetermined amount of a binding partner for said analyte or labelled analogue is immobilised;

c) allowing the sample, labelled binding partner for said analyte or a labelled analogue of said analyte and labelled control reagent to flow through a control zone which is spaced from said detection zone, and in which a binding agent which binds the labelled control reagent is immobilised, said binding agent being present in an amount sufficient to give a similar signal to that which occurs in the detection zone when all binding sites are fully occupied by either the labelled binding partner for said analyte or the labelled analogue of said analyte;

d) detecting the label density in the detection zone (T), and the label density in the control zone (C) and comparing these densities.

As used herein, the expression "analogue of the analyte" refers to a moiety which behaves in a similar manner to the analyte in the context of the assay system. Hence, it may comprise the analyte itself, or a variant or fragment of the analyte, such as an epitopic fragment, which will interact with specific binding partners used the assay as the analyte itself would.

The analogues may comprise additional moieties as required. For instance, where in the case of (a) above, an analogue of the target analyte is immobilised in the detection zone, these analogues may be coupled, for instance by covalent bonding to a spacer molecule such as bovine serum albumin. A particular example of the use of such a spacer moiety in relation to progesterone as an analyte is described in EP-A-0282192.

Using this arrangement, when the label density in the detection zone (T) is similar or equal to that in the control zone (C), the sample contains no analyte. Thus the control is set at essentially the "zero" point for the analyte. However, when the label density in the detection zone is less the label density in the control zone (C), at least some analyte is present in the sample.

The relative densities of the signals in the detection and control zones may be interpreted in various ways, in order to provide an estimate of the amount of analyte present in the sample. Label density may be measured using parameters such as reflectance (where generally the greater the level of reflectance from the support, the lower the label density), or emissions such as fluorescence (where the greater the fluorescence level, the greater the label density).

In particular however, the determination is made by measuring the label density in a reference zone (R), where no binding partners are immobilised, as well as the density in the detection zone (T) and the density in the control zone (C). The ratio of the difference between signals in the reference zone (R) and detection zone (T) to the difference between the signals in the reference zone (R) and control zone (C) will provide an indication of the amount of analyte present in the sample.

This may be represented by the formula R−T/R−C, or T−R/C−R depending upon the manner in which the label density is measured, for example whether it is read on the basis of reflectance or emission.

For instance, where the parameter measured as an indicator of label density is emission for example from a fluorescent label, or absorbance of light by a coloured label, then the absolute value of the signal in the detection and control zones will generally be numerically higher than that in the reference zone (R), and so the formula T−R/C−R may be easier to refer apply.

In a case where reflectance is used to evaluate label density, then it may be expected that the reflectance in the reference zone (R), where there should be relatively insignificant amounts of label, would be numerically higher than that in the detection zone (T) or control zone (C), where the presence of label will generally reduce reflectance as compared to that of the support. Therefore, the value of the signal will be appropriately measured using the formula R−T/R−C.

Application of these formulae will allow the amount of target analyte present in the sample to be determined at least in a semi-quantitative manner.

Suitably the reference zone is approximately equidistant between the detection zone and the control zone on said solid support.

The label densities are suitably measured automatically using an appropriate signal reading device, and the results processed using a suitably set or programmed data processing device.

By utilising specifically a competitive assay format, combined with a control set approximately at the "zero point", the results are relatively easy to interpret. Any difference in the label densities found at the detection and control zones will be indicative of the presence of analyte in the sample. Furthermore, the highest possible density signal will be known in this case, and so any automatic density reading devices can be set accordingly.

In particular, the determination of high levels of analyte can be carried out more accurately than in the sandwich type assay format, as the assay does not rely on the capture of high levels of reagent. In a sandwich assay, capture becomes less reliable as sites become filled. However, in a competitive assay, the more analyte there is present, the less signal is produced, so that a clearer indication of analyte content is achieved.

The determination may be semi-quantitative, in the sense that the results are interpreted to determine whether the amount of analyte present is above a certain level. This can be done by automatically setting any reading device to indicate whether the value of the formula R−T/R−C (or where applicable T−R/C−R) exceeds a certain value, which can be expressed as a percentage or a reciprocal of percentage. Thus for instance, in a test where a permitted analyte concentration in a product is a given percentage, such as 50%, the reader can be set so that when this value of reduction of signal in the detection zone is achieved, the reader will automatically indicate this, which may mean, in the case of a foodstuff or the like, that the product being tested is not acceptable, or has failed the test.

Alternatively, the results may be utilised as part of a quantitative assay, to provide an estimate of the absolute amount of the analyte. This may involve also running a range of standards, having known concentrations of analyte, in the sample, so as to assess precisely what the signal obtained in the detection zone indicates in terms of concentration of analyte. In particular, however, the determination is semi-quantitative.

The label used is preferably a visible label that can be used to give a signal, which is readable using a reflectance reader, and most preferably a portable or desktop reflectance reader. Examples of such labels, particulate labels such as latex, gold and silica.

Other visible labels such as fluorescent or chemiluminescent labels that may be detected using a fluorimeter or luminometer respectively may be employed.

Alternatively, the labels may comprise radioactive, labels that may be detected using a radiation detector.

Preferably the same label is used for the analyte specific binding partner or the labelled analogue of the analyte, and the labelled control reagent. However, this may not be essential, provided that the assay device is optimised so that similar signals, in the sense that a signal reader will detect them as being of similar intensities, are achievable within the control and detection zone.

"Similar" in this application means the same or substantially the same, for example, similar signals will be those where the difference in signal intensity is less than 20% of the highest signal value, for example, less than 10% of the highest signal value, suitable less than 5% of the highest signal value, and preferably less than 2% of the highest signal value. Most preferably, the term "similar" means the same.

For instance, particulate labels on the labelled binding partner for the analyte or the labelled analogue of the analyte may be of a different size to particulate labels on the labelled control reagent. In this case, fewer of the larger labels will give a signal of similar intensity to that obtained using smaller labels. As a result, the concentration of the immobilised reagents in the detection and control zones must be adapted accordingly.

Similarly, the labels may be of different colours, or shades of the same colour, provided only that they can give rise to signals which are seen to have similar densities, albeit at different concentrations. Calibration charts may be available or can be prepared using conventional methods such as those illustrated in the examples hereinafter, so that selection of suitable combinations of labels and concentrations are achievable.

Preferably the detection zone contains an analogue of the analyte immobilised thereon, and a labelled binding partner for the analyte is the diffusibly bound partner therefore. This is because analogues of the analyte can be more readily applied to solid supports in controllable amounts. In addition, the number of binding sites corresponding to analyte is more consistent, than where binding partners such as antibodies are immobilised, as it is possible in the latter case, that labelled reagent can occupy more than one site.

Preferably, during the test procedure a known volume of sample, which is suitably an aqueous solution, is added to the solid support, in particular when a semi-quantitative or quantitative result is required.

In the manner conventional in dipstick assays, the liquid sample travels along the support member, releasing diffusible reagents as it goes, and carrying these and any analyte through the support, including through both the detection and control zones.

The accumulation of labelled binding partner for the analyte or labelled analogue of the analyte in the detection zone (T) is inversely proportional to the amount of target analyte in the sample. For example if high levels of target analyte are present in the sample being tested, then the target analyte will bind to the labelled binding partner of the analyte, preventing it from binding to the analogue of the analyte immobilised at the detection zone. Alternatively, where the diffusible element of the assay is a labelled analogue of the analyte, high concentrations of analyte will compete with the labelled analogue for binding to the immobilised binding partner, reducing the quantities of label which will be accumulated in the detection zone. This results in a low or lack of signal at the detection zone (T). Thus the more target analyte is present in a sample the lower the signal will be at the detection zone, whereas if no target analyte is present in the sample being tested a strong signal will be generated at the detection zone due to the labelled target binding partner, binding to the analogue of the target analyte which is immobilized in the detection zone.

The labelled control reagent is however free to bind specifically to the binding agent immobilised in the control zone and accumulate to give the desired signal. The assay is dynamic and continues to develop at both the detection and the control zones, until substantially all the available material has bound.

Suitably an excess of mobile labelled reagents will be present so that all available binding sites within the control zone will be occupied during the assay, as will all the available binding sites in the detection zone, where no analyte is present in the sample.

Specific reagents used in the assay device will be selected so as to ensure that the particular target analyte is detected as is well known in the art. The target analyte may be any analyte for example a chemical reagent which may be organic or inorganic, and which optionally comprises a hapten, a protein, a polypeptide, a microorganism or a nucleic acid sequence.

In particular, the analyte is a hormone such as a fertility hormone like progesterone or a stress hormone such as cortisol. When progesterone is the analyte, a particular example of an assay would include progesterone or an analogue linked to the support in the detection zone, by way of a spacer such as bovine serum albumin (BSA) as described for example in EP-A-282192.

However, there is a wide range of applications of these type of tests across the entire field of diagnostics and analysis. Detection of marker proteins or hormones can be diagnostic of certain disease conditions in humans or animals, and the presence of drugs or drug residues may also be required to be detected, for example, in animal husbandry, forensic medicine or in the testing for banned or prohibited drug substances.

Alternatively, the analyte is a chemical reagent, for instance a small molecule, which suitably comprises a hapten. Small molecules will generally comprise a single recognisable binding site. Typically they will have a molecular weight of less than 1 kDa.

The method of the invention may be particularly useful in the detection of agrochemicals, both active agrochemicals and as residues.

For instance, the method described above can be utilised in agriculture to detect particular pests or pathogens on crop plants, such as fungal antigens or viral infections. They may also be utilised to detect pesticide residues on crops.

The applicants have found however that analytical techniques of this type can be applied more widely and in particular can be used to assist in the growing process.

Thus in a particular embodiment, there is provided a method for detecting the presence of amount of an active agrochemical contained within plant tissue, said method comprising extracting said plant tissue into a solvent in which said active agrochemical is soluble, and detecting active agrochemical within said sample using a method as described above.

As used herein the term "agrochemical" refers to any chemical reagent which has a desirable effect on crops. They may be organic or inorganic molecules, as well as proteins, polypeptides and peptides. Most typically, the agrochemical will comprise small organic molecules. Agrochemicals may comprise herbicides, fungicides, insecticides and plant growth regulators, which may be applied to growing plants or as seed treatments. In some cases, the plants themselves may be genetically engineered to express the agrochemical, for instance, an insecticides based upon *Bacillus thurigenesis* derived proteins (Bt).

In accordance with a particular embodiment of the invention, only active agrochemical is detected and not any residues. This may be achieved by conducting an assay that tests for activity, but is more conveniently carried out by detecting the active chemical itself. Most agrochemical compounds, or indeed any biologically active material, such as therapeutic or prophylactic compounds, may comprise active chemical groups or elements that are "used up" when the biological activity is initiated. For example, agrochemicals may contain a "warhead" which may be broken down after use, for example by metabolism within a plant, or by degradation as a result of exposure to light or to conditions found in the soil or the like.

The mechanism by which many biologically active materials such as agrochemicals are degraded is frequently well understood, and so therefore, it is generally clear what particular chemical elements within the molecule is required for the biological activity, and which elements are degraded once the agrochemical has been used. By assaying for one of these elements, the presence of active molecules only will be detected.

By detecting the biologically active material such as the active agrochemical in a semi-quantitative manner as described above, it is possible to determine whether the amount of the biologically active material within a particular sample is of a level which is sufficient to provide the desired activity. This means that the results can be used to determine whether further application of the biologically active material agrochemical, is required in order to achieve the desired result, which in the case for example of an agrochemical is for the plant to benefit from the effect thereof.

The method is suitably applied to any convenient sample of plant tissue, and this will vary depending upon the nature of the crop and the agrochemical being treated. In many cases however, suitable plant tissue is leaf tissue.

It may be desirable, for example in the case of insecticides which are active against biting pests, to determine how much active material remains on the surface of the leaf.

Generally however, where the agrochemical has a systemic effect on the plant, it will be necessary to remove any material which remains on the surface of the leaf before analysing the tissue. This can be easily done by first subjecting the leaf tissue to a washing step so as to remove agrochemical from the surface thereof. Thereafter, a sample can be generated for example by macerating or otherwise disrupting the leaf structure, and detecting material in the sample obtained. In this way, only agrochemical which has penetrated the leaf is detected.

A particularly convenient way of obtaining such a sample is to add a sample of the leaf to a container, for example a bottle, which contains a solvent, and a solid such as ball-bearings, and shaking the container to allow the solid to disrupt the leaf, allowing agrochemical to be dissolved into the solvent. This then forms the sample for analysis.

Alternatively, the plant tissue is root tissue. This may also be suitable in the case of systemically acting agrochemicals, as well as seed treatments. It may be particularly suitable for testing for agrochemicals which are intended to protect the roots from attack, for example, for nematicides or fungicides.

When the biologically active material is other than an agrochemical, suitable sample preparation methods will be those generally known in the art. For instance, biological fluids such as urine, plasma and milk may require little preparation, whereas other samples may be prepared by applying concentional extraction techniques.

Where the assay utilises a labelled binding partner for the analyte and the analyte is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or Van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid. Conversely, where the binding partner may comprise the acid part of the reactive pair.

Where the analyte is or comprises a hapten or a protein antigen, the binding partner may comprise an antibody or a binding fragment thereof, which may be monoclonal, polyclonal or recombinant, but preferably is monoclonal. Where the analyte is a hormone or enzyme, the labelled binding partner may comprise a labelled receptor for the analyte. However, where the analyte is itself an immunoglobulin, and in particular, an antibody, the labelled binding partner may also comprise for instance, an antigen or recombinant antigen, as well as anti-antibody immunoglobulin such as antisera.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

For example, where the analyte is a biologically active material such as an active agrochemical as discussed above, specific reagents used in the assay device will be selected so as to ensure that the particular target biologically active material is detected as is well known in the art. The biologically active material may be any active chemical such as an agrochemical, for example a chemical reagent which may be organic or inorganic, and which optionally comprises a hapten, a protein, a polypeptide, a microorganism or a nucleic acid sequence. Most preferably the biologically active material is a chemical reagent, for instance a small molecule, which suitably comprises a hapten. Small molecules will generally have a single antibody binding site. Typically they will have a molecular weight of less that 1 kDa.

For instance, where the assay utilises a labelled binding partner for the active agrochemical and the active agrochemical is a chemical reagent, the binding partner may comprise any other reagent which reacts with or otherwise becomes associated with the chemical reagent, either because it forms covalent or ionic bonds with the reagent, or by the formation of other interactions, such as hydrogen bonding or Van der Waals interactions. For example, where the chemical reagent is an acid, the binding partner may comprise an alcohol or an amine that forms an ester or amide with the acid under the sorts of conditions found in the test. Alternatively the binding partner may comprise a base that forms a salt with the acid. Conversely, where the binding partner may comprise the acid part of the reactive pair.

Where the analyte is a biologically active material such as an active agrochemical is or comprises a hapten or a protein antigen, the binding partner may comprise an antibody or a binding partner therefore, which may be monoclonal, polyclonal or recombinant, but preferably is monoclonal.

Where the analyte is a biologically active material such as an active insecticide, for instance, an organophosphate pesticide, which has activity as a nerve agent, the binding partner for it may comprise a suitable receptor or binding fragment thereof. Particular receptors may comprise acetyl cholinesterase receptors.

Antibodies or binding fragments to small molecules such as haptens, are generated by attaching the molecule to an immunogenic reagent and administering this to an animal such as a mouse or rabbit. Antibodies are then harvested from the animal in the usual way. Monoclonal antibodies are obtained by fusing spleen cells to hybridoma cells, and selecting those which bind the hapten, using routine procedures.

The hapten used will suitably comprise the active chemical group, for instance an agrochemical or a fragment or functional group or "warhead" which is present in the active form of the agrochemical but not in spent material such as material which has been metabolised, for example by the plant and is, as a result, no longer active.

Suitable examples of binding agents which may be used to detect agrochemicals and their preparation are described for example in WO01/42787, which describes antibodies for neonicotinyl insecticides, EP-A-1043336, which describes antibodies which are specific for imidazolinone herbicides, J. K. Lee et al., J. Agric. Food Chem. 2003, 51, 3695-3703 which describes antibodies for organophosphorus insecticides, in particular acetphate, J. F. Lawrence et al. J. Chromatography (1996) 732, 277-281 which describes antibodies to phenylurea herbicides, and J. F. Lawrence et al. J. Chromatography (1996) 752, 147-154 which describes antibodies to triazine herbicides.

Where these references describe polyclonal antibodies, for the purposes of the present invention, these are preferably used to generate monoclonal antibodies using conventional techniques.

Where a particulate label is used, the binding partner is suitably coated all over the particle, which maximises the chances that the particle will take part in any binding action possible, either with the analyte or with the immobilised analogue of the analyte in the detection zone.

Similarly, where the assay utilises the analyte or an analogue of the analyte, this also may be coated onto a particulate label for maximum sensitivity.

The amount of reagent immobilised in the detection zone is controlled so as to generate the desired signal.

The analogue of the target analyte used, in particular as the immobilised element in the detection zone, could be a fungal extract containing the target analyte where this is of fungal origin, or a protein-hapten conjugate where the hapten is the analyte or a derivative of the analyte.

In a particular embodiment, the solid support may contain more than one detection zone each containing an immobilised analogue of a different analyte, or a binding partner for a different analyte, so that the method could be conducted to detect the presence of more than one analyte in a sample. In such cases, additional diffusible labelled binding partners for each additional analyte will be provided on the support. In such cases, it would be preferable to include a further control zone, and a corresponding labelled diffusible further control reagents, to provide individual comparative analysis, in the same way as described above for the first detection and control zones. For example, a further reference zone ($R^1$), which, in this instance will be located, preferably approximately equidistantly, between the further control zone and the further detection zone will be provided and the signal in this zone measured for analytical purposes.

The control reagent and the binding partner therefore may be selected from any available reagents, provided only that neither of these binds the analyte, nor any analogue or binding partner for the analyte utilised in the assay. Therefore, the control reagent and the binding partner therefore may comprise an antibody/antigen pair, or a generic binding pair, such as streptavidin and biotin. Where biotin is used as the binding partner for the labelled control reagent, it may be administered in any convenient form, for example as a biotinylated protein such as biotinylated bovine serum albumin (BSA) or derivatives thereof, as illustrated hereinafter.

Any antibody used as part of the antibody/antigen pair (either as antibody or antigen) may be monoclonal, polyclonal or recombinant, and preferably a monoclonal antibody, or it may comprise binding fragments of any of these. In a particular embodiment, the labelled control reagent is a labelled antibody such as a labelled anti-sheep or anti-rabbit antibody, and the binding partner in the control zone is a polyclonal antibody or anti-sera for the antibody.

The solid support may be in the form of a single self-supporting unit, comprising a sample addition region, and a region containing the diffusible elements upstream of the detection and control zones. Alternatively, it may be modular in nature, and contain at least one additional element, such as reservoir unit and/or a sink unit.

Suitably the solid support comprises a reservoir unit preferably formed from an inert material such as a glass fibre. This is fluid contact with the solid support and arranged in an area for sample addition and/or a particle reservoir. The reservoir unit may be in the form of two distinct parts for example a sample pad for sample addition, and conjugate release pad which acts as a particle reservoir or may be in the form of a single composite pad that performs both of the above functions.

The solid support is a support unit in which the detection zone (T) and the control zone (c) are located. The solid support comprises at least one control zone (C) and at least one detection zone (T). As used herein the term "solid support" shall be taken to mean any material for example a membrane or wick along which a sample can travel.

If desired, a functional marker zone (which corresponds essentially to a conventional control zone), which has immobilised therein a reagent which binds either the labelled binding partner for said analyte or the labelled analogue of said analyte, whichever is present in the assay. Development of a signal in this zone will provide additional confirmation that the assay has proceeded correctly.

A conventional nitrocellulose membrane is a preferred solid support for use in the method of this invention. It may be pretreated to block unused sites, as it conventional in the art.

The sink unit if present may be formed from an absorbent material to ensure that added sample is drawn, preferably by capillary action, from the reservoir unit across the detection zone (T) and control zone (C) towards the sink unit until the solid support is saturated.

In a preferred embodiment of the invention the solid support is housed within a non-absorbent or laminate casing.

Devices for use in the method described above form a further aspect of the invention. Therefore, in a second aspect, the invention provides apparatus for the determination of a target analyte in a sample, said apparatus comprising:

a solid support capable of allowing lateral flow of liquid therethrough, which support has diffusibly arranged thereon, (i) either (a) a labelled binding partner for said analyte or (b) a labelled analogue of said analyte, and (ii) a labelled control reagent, and wherein the support further comprises a detection zone on said solid support, wherein in the case of (i)(a) above, a predetermined amount of an analogue of the target analyte is immobilised, or, in the case of (i)(b) above a predetermined amount of a binding partner for said analyte or labelled analogue is immobilised, and a control zone which is spaced from said detection zone, and in which a binding agent which binds the labelled control reagent is immobilised, said binding agent being present in an amount sufficient to give a similar signal to that which occurs in the detection zone when it is fully occupied by either the labelled binding partner for said analyte or the labelled analogue of said analyte.

Suitably the support element comprises a membrane as described above. It may comprise a reservoir and sink unit, and be located in a casing, also as described above.

The amount of binding agent present in the control zone must be such that it produces a similar signal to that which occurs in the detection zone when it is fully occupied by either the labelled binding partner for said analyte or the labelled analogue of said analyte. This is preferably determined by routine calibration or testing methods. For instance, the apparatus described above is set up with predetermined amounts of appropriate reagents immobilised in the detection and control zones. Then a liquid matrix, such as a solvent for example water, which optionally contains a buffer, is applied to the support to allow the diffusibly bound reagents to migrate along the support. In the absence of analyte, the signals resulting from the detection and control zones should be similar, and if they are not, then the predetermined amounts of the immobilised reagents need to be adjusted until they are.

It is usually important, when carrying out this calibration method that the liquid matrix used is the same as that in which the ultimate samples are going to be tested, as the nature of the matrix can impact on signal generation. Thus, where for example, the test is to be used on an agrochemical sample, prepared as described above, using a solvent (which may be an aqueous solvent, or a solvent containing extractants or the like), it is preferable that this solvent is used as the liquid matrix in the calibration work, to eliminate matrix effects.

Examples of such calibration methods are given hereinafter.

In a particular embodiment, the apparatus further comprises a signal reading unit which is set to interpret the results obtained with a sample is applied to the apparatus as described above, and the assay allowed to run. A particularly suitable signal reading unit comprises a portable reflectance reader, which allows the assay to be carried out, and the results calculated on site, where testing is required, for instance in a food monitoring operation.

The reader is suitably set to make the calculation R–T/R–C automatically, and if desired, to provide an indication as to whether a particular value has been exceeded or otherwise.

Suitably the reader will be adapted so that the solid support, in particular within its casing, is inserted into an appropriate slot in the reader device, so that the control, reference and detection zones become aligned with signal reading elements. This can be achieved if the device includes a plurality of reading elements, but may be most conveniently achieved by scanning then length of the support unit with a reflectance reader, once the signals have had an opportunity to fully develop.

A particularly suitable reading device is obtainable from Otsuka (Japan).

The invention will now be particularly described by way of example and with reference to the following figures in which.

Figure 3:
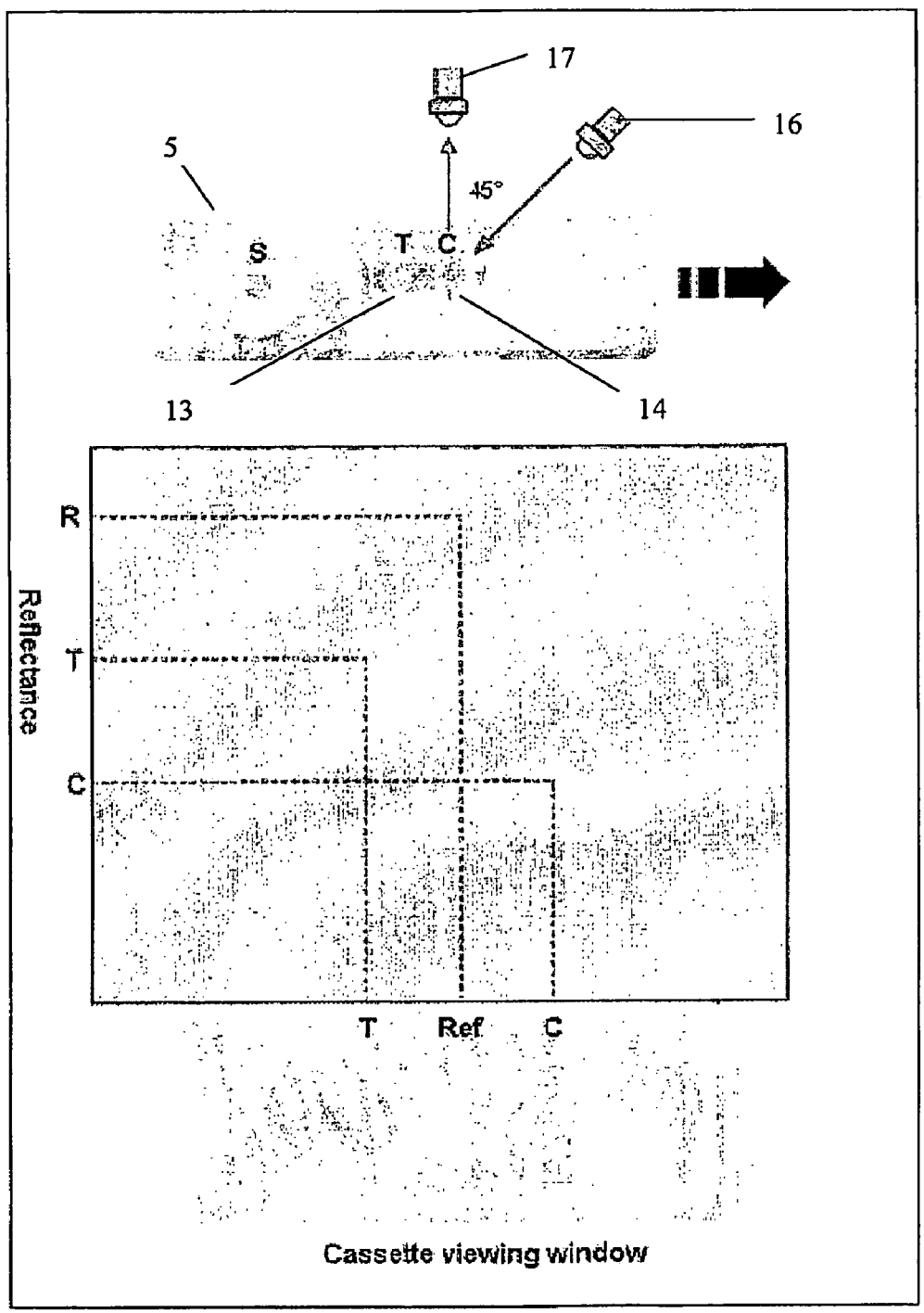
Figure 4:
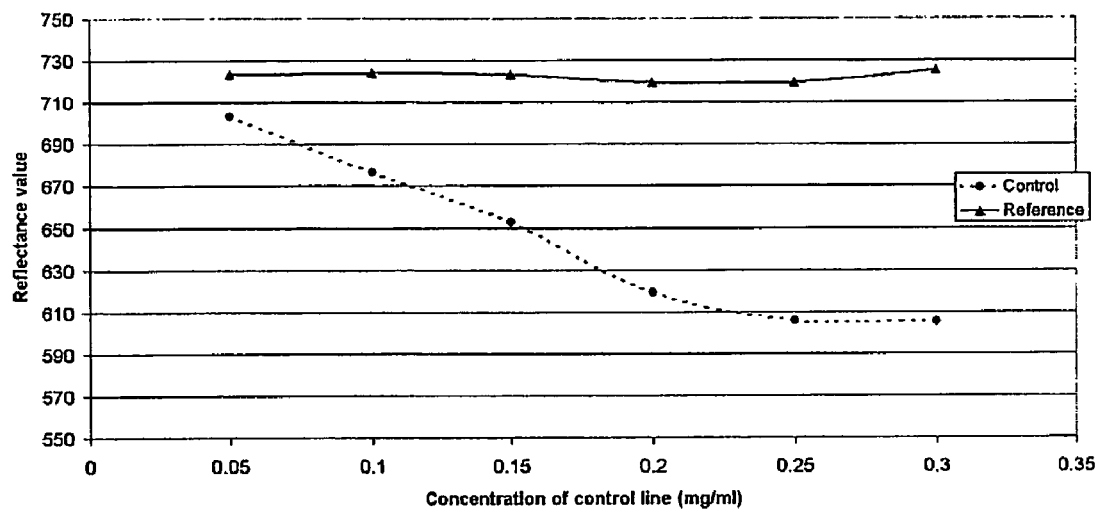
Figure 5:
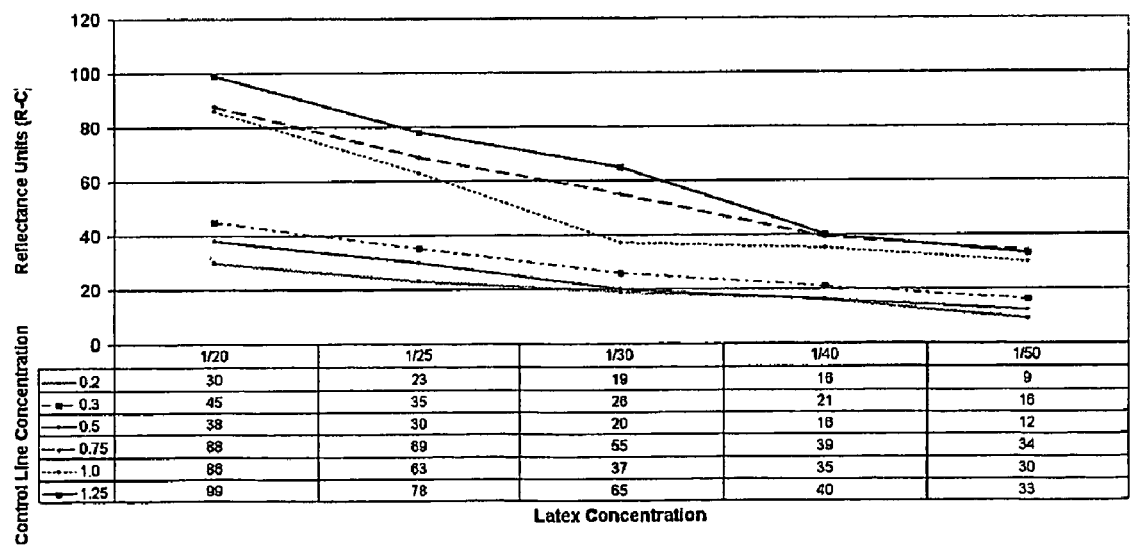
Figure 6:
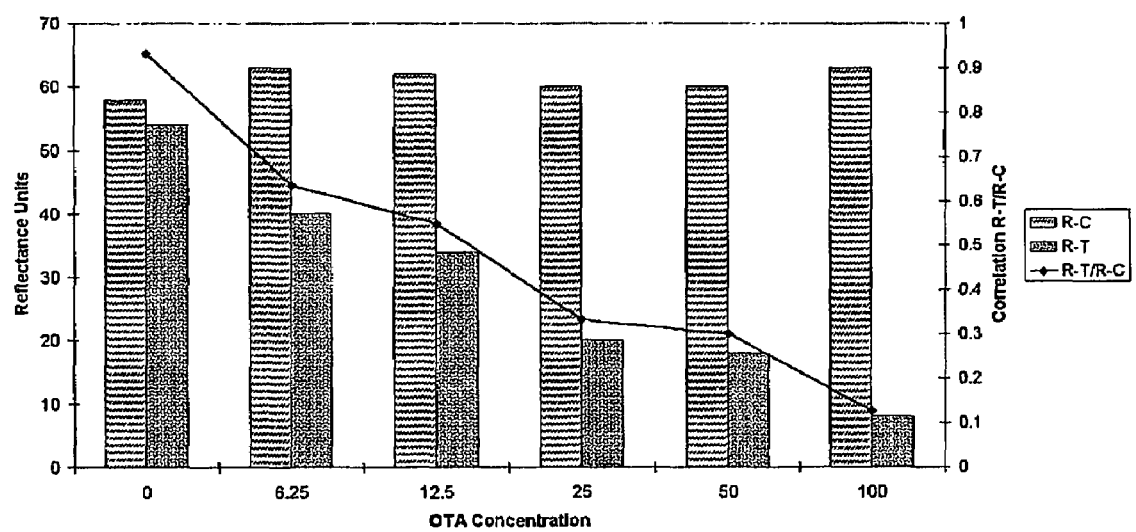

FIG. 3, which is a diagrammatic representation of the reading of a signal from an assay of the invention, including a graph to show the signal;

FIG. 4 shows the reflectance signals obtainable from a control system based upon sheep/anti-sheep antibodies and how these vary vs the signals in a reference zone depending upon the concentration of the control line;

FIG. 5 shows the difference in the reflectance signals obtainable from a reference zone (R) and a control zone (C) varies with the concentration of the control line and the concentration of the labeled control reagent, using a control system based upon biotin/streptavidin;

FIG. 6 is a graph demonstrating reflectance units and % correlation of T and C lines obtained using the method of the invention, on a range of Ochratoxin A (OTA) standards (0-100 ppb) in extraction buffer.

Figure 7:
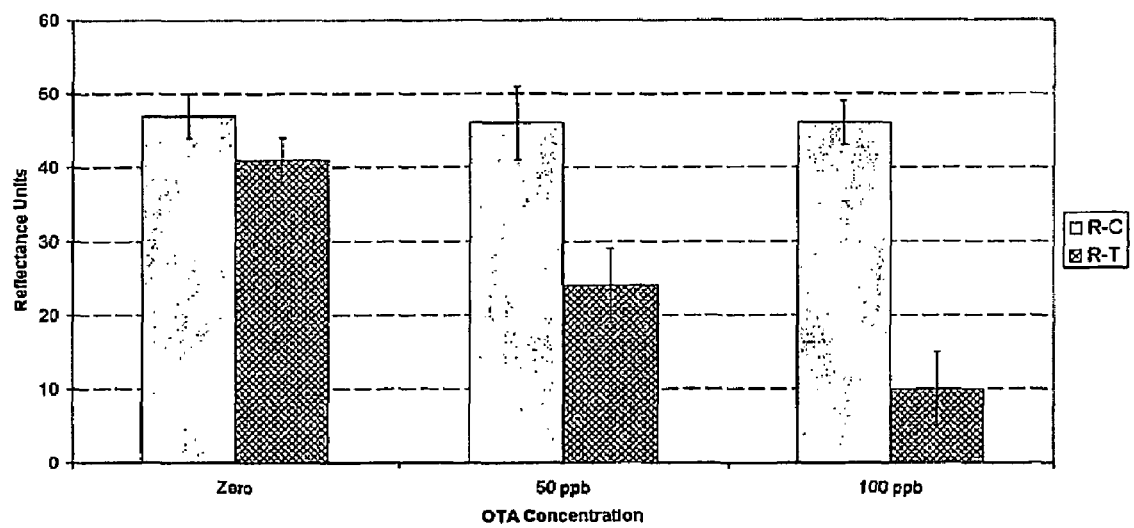

FIG. 7 represents the constant R–C values and changes in R–T values, when samples contain 50 or 100 ppb OTA, for the experiment of FIG. 6.

Figure 8:
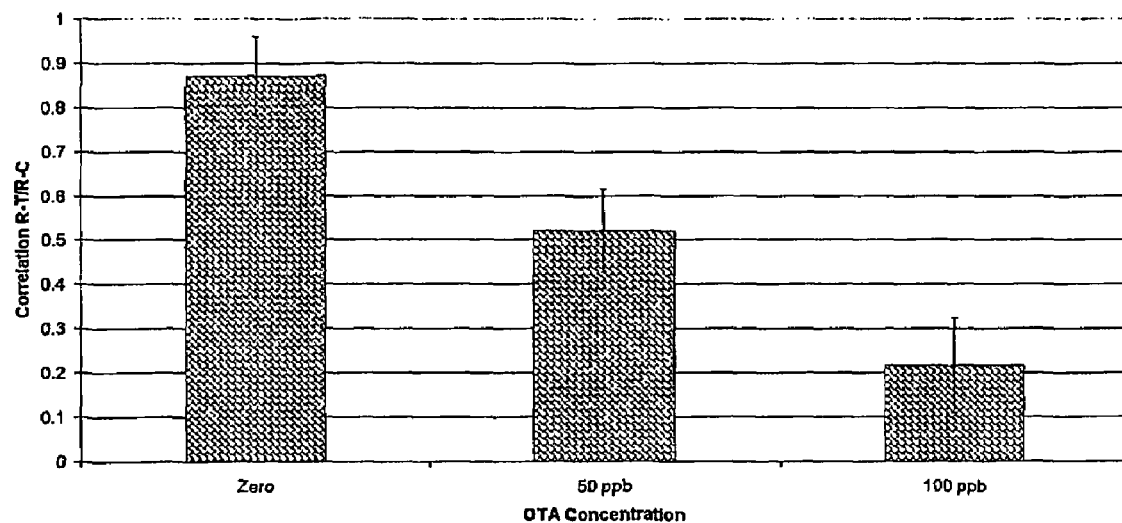

FIG. 8 represents the same data as that of FIGS. 6 and 7 as a correlation of R–T/R–C.

Figure 9:
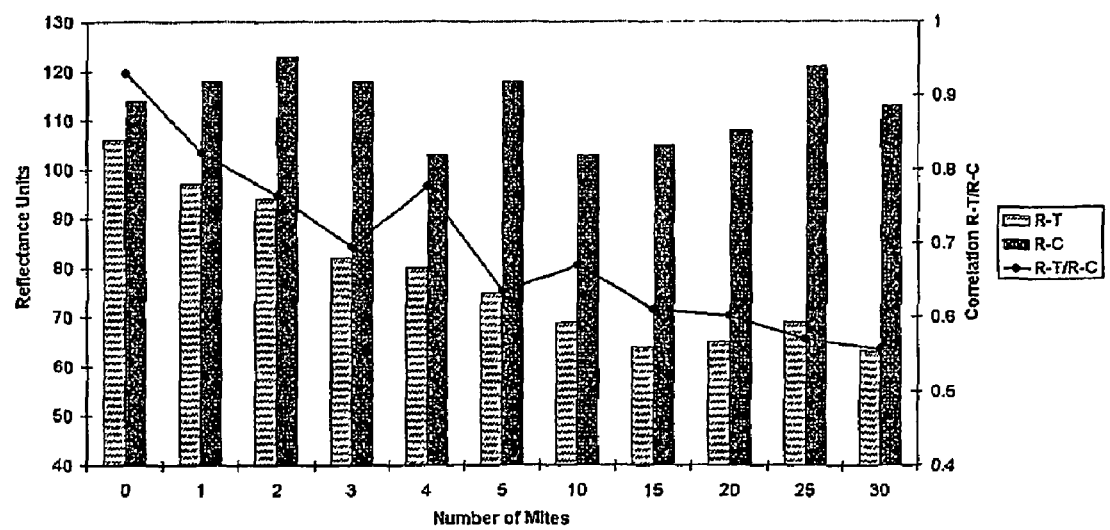

FIG. 9 is a graph showing the results obtained when the method of the invention was applied to the detection of *Acarus siro* (flour mite), where the results are presented as both individual reflectance units of C and T zones, in relation to the reference zones (R), and also the correlation between the both.

Figure 10:
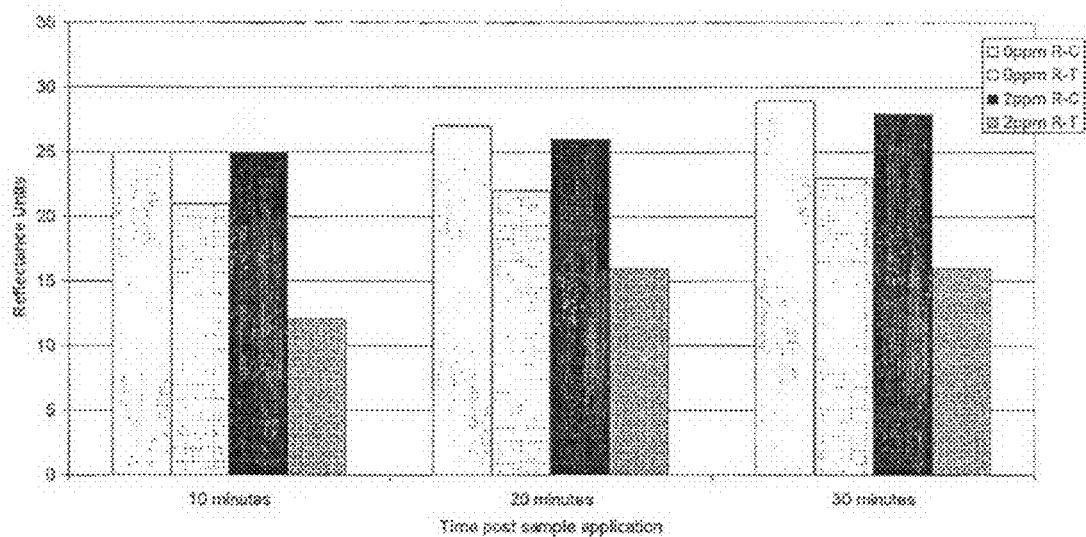

FIG. 10 is a graph showing the results of the application of the method of the invention to the detection of the drug, nicarbazin, and shows control (R–C) and target (R–T) reflectance units for two sample concentrations (0 ppm and 2 ppm nicarbazin) at 10, 20 and 30 minutes post sample application.

Figure 11:
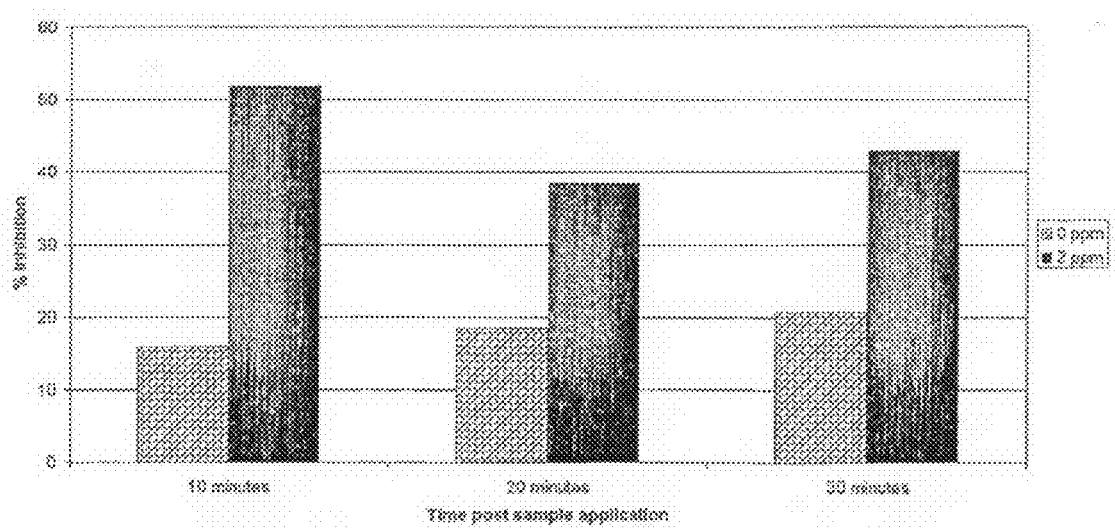

FIG. 11 is a graph showing the % inhibition of target line in relation to the control, calculated as 100−((R−T/R−C)×100), against time post sample application, obtained in the same experiment as that of FIG. 10.

Figure 12:
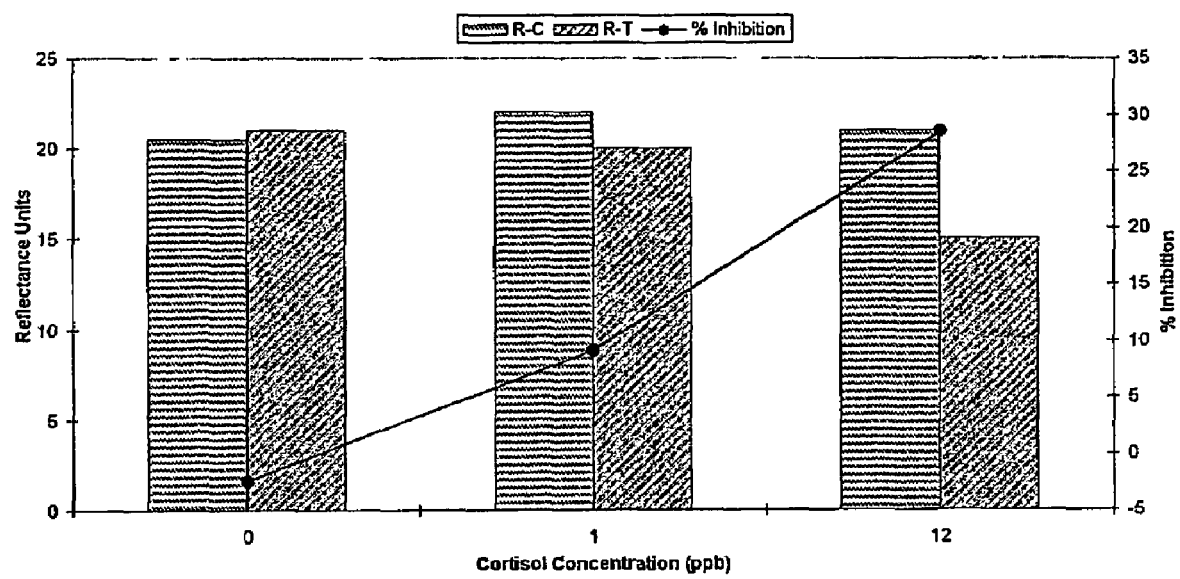

FIG. 12 is a graph relating to the results obtained using the method of the invention to detect cortisol, which shows individual reflectance units for C and T, and % inhibition of T in relation to C for a range of standards in buffer (0, 1 and 12 ppb).

EXAMPLE 1

Assay Devices

Figure 1:
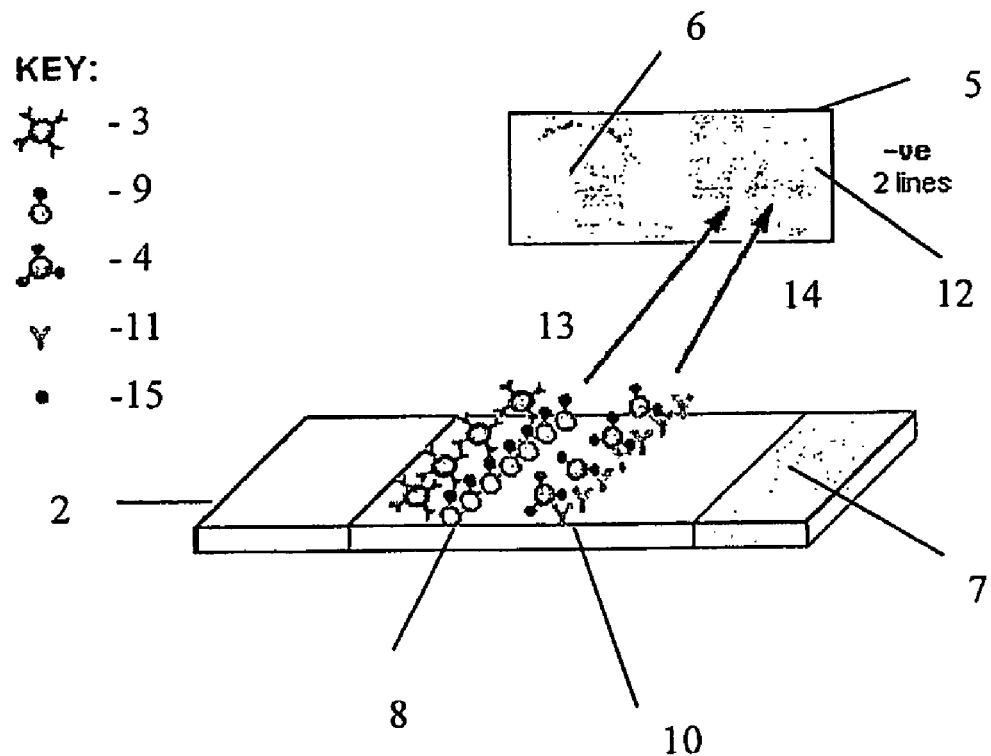
FIG. 1, is a diagrammatic representation of an assay embodying the invention, including a diagram which shows a solid support for use in the method of the present invention, a key showing the elements contained, and a representation of an actual apparatus showing two negative lines indicating the absence of target analyte.
Figure 2:
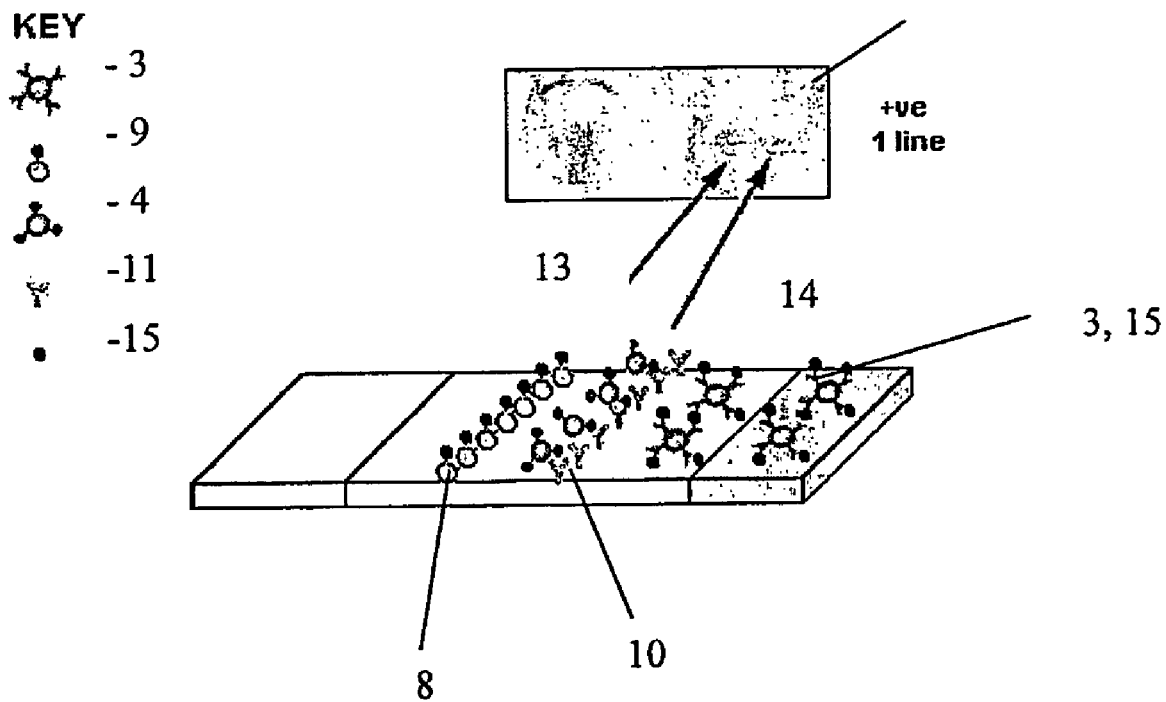
FIG. 2, is similar to FIG. 1, but in this case, it illustrates a positive assay in which analyte is present in the sample.

The illustrated assay device of FIGS. 1 and 2 shows a solid support (1) which includes a release pad (2) to which sample is applicable, and which contains the diffusible elements, which in this case comprise an analyte specific monoclonal antibody coated particle (3) and a control reagent coated particle (4). The support (1) is contained within a casing (5), which has a sample application opening (6) adjacent the release pad (2).

The support (1) further comprises an absorbent pad (7) which acts as a sink unit at the remote from the release pad (2). Intermediate the release pad (2) and the absorbent pad (7), are arranged a detection zone (8) in which are immobilized an analogue of the target analyte (9), and a control zone (10) in which a control specific antibody (11) is immobilized.

The casing (5) is further provided with a viewing window (12) allowing the detection zone (8) and control zone (10) to be viewed through the casing (5).

When, in the case of FIG. 1, an aqueous sample which does not contain analyte, is applied to the release pad (2) through the opening (6), it collects the particles (3) and (4), and wicks along the solid support (1) towards the absorbent pad (7). As it passes the detection zone (8), the analyte specific monoclonal antibody coated particle (3) binds to the immobilized an analogue of the target analyte (9) and so develops a signal line (13).

As the sample passes through the control zone (10), the control reagent coated particles (4) become bound to the immobilized control specific antibody (11), thus developing a control line (14).

The assay is set up so that in this case, the signal line (13) and the control line (14) are of equal intensity.

When such a device is used instead with a sample containing target analyte (15) (FIG. 2), the sample meets first the analyte specific monoclonal antibody coated particles (4) and the target analyte (15) becomes bound thereto. This blocks the antibody binding sites on the particles (4) which are therefore unable to bind in the detection zone (8), and so pass on through the control zone (10) into the absorbent pad (7). As a result, the signal line (13) fails to develop, at least not to the same extent as the control line (14).

This difference is distinguishable, in particular when the signals are read using a reflectance reader as illustrated in FIG. 3.

In the illustrated device, a light source (16) directs a beam of light onto the support (1) through the viewing window (12). A light detector (17) is arranged to detect light reflected at 45 degrees to the incident beam. By scanning the light source (16) and the light detector (17) along the length of the support, a measure of reflectance vs. position in the sample cassette will be represented by a graph as shown in FIG. 3B.

This graph illustrates also the positions at which the measurements C, R and T are taken, so as to apply the equation R−T/R−C, and so provide semi-quantitative results, in a reliable, rapid and simple manner.

EXAMPLE 2

Sheep/Anti-Sheep Internal Control

An internal control system was developed based on a sheep sera coated latex particle as the labelled control reagent, and the respective binding partner, in this case anti-sheep polyclonal antibody, deposited as a line at the Control zone. This internal control system was incorporated into an existing competitive LFD system. In accordance with the method of the invention, the reflectance value obtained using the internal control system needs to be adjusted to give the same reflectance as obtained from the target line, when a negative sample was analysed.

To manipulate the internal control reflectance value both latex concentration and or line concentration, can be manipulated. In this example we demonstrate how changes in reflectance occurs as line concentration varies.

A housed lateral flow device was assembled following normal best practices. The internal control was developed using a 0.4 µm blue latex particle, passively coated with Negative Sheep Sera (Sigma), using 2 mg/ml concentration, following established methods. Anti sheep polyclonal antibody was deposited using a Biodot dispenser at working dilution of 0.05-0.3 mg/ml, onto nitrocellulose membranes.

Test strips were assembled onto cards and then plastic housings. Each test was analysed using a standard buffer by the addition of 75 ul. Each test was run for 8 minutes and each device read for reflectance using a portable LFD reader (Otsuka). In this example the results are presented as reflectance units for the reference area (R) and control line (C).

The results, shown in FIG. 4 indicate that by varying the control line concentration the reflectance value for R is constant whilst the C values decrease from very weak line (703 reflectance units) to saturated blue lines (605 reflectance units) at line concentration of >0.25 mg/ml.

EXAMPLE 3

Biotin/Streptavidin Internal Control

An additional internal control system was developed, based on a streptavidin coated latex particle as the labelled control reagent, and the respective binding partner, in this case, biotin, in the form of biotinylated amido caproyl BSA, deposited as a line at the Control zone. This internal control system was then incorporated into an existing competitive LFD system. The reflectance value obtained using the internal control system was adjusted to give the same reflectance as obtained from the target line, when a negative sample was analysed. To manipulate the internal control reflectance value both latex concentration and or line concentration, can be manipulated. In this example we demonstrate changes in reflectance as line concentration varies.

A housed lateral flow device was assembled following normal best practices. The internal control was developed using a 0.43 µm blue latex particle, passively coated with a bovine serum albumin (BSA)—streptavidin conjugate, at 1 mg/ml total protein concentration, following established methods. The latex particles were diluted following sensitisation ⅕ in a sucrose/BSA deposition buffer. This was further diluted and applied onto the conjugate release pad in a range of dilutions of from 1/20-1/50.

A BSA-biotin conjugate was applied as the control line at varying concentrations 1.25-0.2 mg/ml, total protein concentration, deposited using a Biodot dispenser onto nitrocellulose membranes, specifically Millipore Hi-Flow 180 membranes.

Test strips were assembled onto cards and then plastic housings. Each test was analysed using a standard buffer by the addition of 75 ul. Each test was run for 10 minutes and each device read for reflectance using a portable LFD reader (Otsuka). In this example the results (FIG. 5) are presented as a correlation, the difference between the relative reflectance units for the reference area (R) and control line (C).

The results shown indicate the change in control line reflectance units is dependent on both latex application concentration and control line concentration. Both these parameters can be modified, to incorporate a control line of suitable density. For example a control density (R−C) of 60 could be obtained using a control line at 1.0 mg/ml and latex at 1/25 or a control line at 1.25 mg/ml and a lower latex concentration of <1/30.

EXAMPLE 4

Test Method and Device for Ochratoxin A

Ochratoxin A (OTA) is a mycotoxin produced by fungi e.g. *Pennicilium verrucosum* and *Aspergillus ochraceus*, in particular during the storage of grain. Ochratoxin A has been shown to be toxic to mammals and as such is monitored in food and grain under legislation. Using a specific OTA mouse monoclonal antibody towards OTA and a BSA-OTA conjugate as the target line, a competitive LFD was developed. To manipulate this assay to be semi-quantitative an internal control system was incorporated. In this case a rabbit sera latex was utilised as the labelled control reagent and an anti-rabbit control line as the binding partner therefor.

A housed lateral flow device was assembled following normal best practices. The internal control was developed using a 0.4 µm blue latex particle, passively coated with negative rabbit sera (Sigma), using 1 mg/ml concentration, following established methods. Anti rabbit polyclonal antibody was deposited using a Biodot dispenser at a pre-determined concentration of 0.25 mg/ml. The internal control latex was mixed with the OTA latex and applied to the device by air jet. The control was deposited during membrane preparation, at the same time as the target line deposition. The membranes are further processed. The processed strips were assembled onto cards and then plastic housings.

Samples were prepared by either dilution of OTA standard in a 20% methanol extraction buffer, or grain sample were processed following a simple extraction method. This comprised of taking 10 g of grain, adding 2 ml of absolute methanol, shaking vigorously, followed by addition of 8 mls of buffer. The samples were allowed to settle before test volume removed.

Each test was analysed by the addition of 75 ul of sample. Each individual test was run for 15 minutes and each device read for reflectance using a portable LFD reader (Otsuka). Reflectance values were obtained for the reference area (R), the control line (C) and the target line (T).

The graph in FIG. 6 demonstrates reflectance units and % correlation of T and C lines on a range of OTA standards (0-100 ppb) in extraction buffer. It can be seen that regardless of OTA concentration the Control line reflectance (R–C) remains constant, however the target line reflectance (R–T) reduces from 55, approximately equal to the control line at zero concentration, to <10 at high OTA concentration (100 ppb). This relationship is shown by the correlation value dropping from ~1 to 0.1 from zero to 100 ppb respectively.

It is this ratio, which can be used as the semi-quantitative measurement.

The graph in FIGS. 7 and 8 represents actual samples analysed post extraction from grain, as described in the method. The first figure, FIG. 7 represents the constant R–C values and changes in R–T values, when samples contain 50 or 100 ppb OTA.

The final figure, FIG. 8, represents the same data as a correlation of R–T/R–C. This ratio could be used as a semi-quantitative guide to concentration of OTA in grain samples.

EXAMPLE 5

Test Method and Device for Detecting Mites

*Acarus siro* (flour mite) is a major pest species commonly found in the storage of commodities, in particular grain. Traditional methods to determine mite infestation levels required laborious laboratory methods, incorporating visual identification and microscopy. The semi-quantitative LFD potentially could replace these existing methods.

The housed lateral flow for this example incorporated the following. A 0.31 μm blue latex particle which is sensitised with a *Acarus siro* specific mouse monoclonal antibody was dispensed on to the release pad of an LFD at a ⅒ dilution, alongside is a 0.41 μm latex particle sensitised with a sheep negative sera, this is applied, at ¹⁄₂₀, at the same time as the *A. siro* particle as a mixed line. The membranes were prepared following established methods, with the control line comprising anti-sheep antibody line, deposited at 0.15 mg/ml, and a target line of purified *A. siro* extracted antigen, deposited at 0.3 mg/ml.

Samples were prepared in the extraction buffer (0.15M NaCl) at a range of mite numbers, and 75 μl of sample added to the completed test devices, and the reflectance values for R, T and C zones determined using the portable reader.

The results are presented in FIG. 9 as both individual reflectance units of C and T zones, in relation to the reference zones (R), and also the correlation between the both.

These results demonstrate that the Control zone reflectance (R–C) is approximately constant irrespective of mite numbers. However the Target zone (R–T) is equivalent to the Control zone when no mites are present but varies in respect to mite numbers. As mite numbers increase the Target Zone reflectance (R–T) reduces. This can also be represented as a change in correlation. An unknown sample could be semi quantified based on the resultant change in correlation, the higher the value, nearer to 1, then the fewer mites present in the sample.

EXAMPLE 6

Nicarbazin Detection Test

Nicarbazin is a veterinary drug product that is used commercially in avian feedstuffs. The properties of this product are beneficial in the growth and development of poultry for meat, however under legislation traces present in the final meat product must not exceed a specified maximum residue limit. This is accomplished by the withdrawal of nicarbazin from the feed schedule at a predetermined stage of growth. A rapid confirmatory test for the determination of nicarbazin levels in avian feed would be beneficial in the implementation and monitoring of such a feed and rearing regime.

A rabbit polyclonal antibody raised to the active ingredient in nicarbazin and an analogue conjugate of the active ingredient were used to develop a competitive LFD. An internal control system was incorporated to enable a semi-quantitative assay to be configured. In this case negative sheep sera latex was used as the labelled control reagent and an anti-sheep polyclonal antibody formed the control line.

A housed lateral flow device was assembled following normal best practices. The internal control was developed using a 0.4 μm blue latex particle, passively coated with negative sheep sera (Sigma), at 2 mg/ml concentration, following established methods. Anti sheep polyclonal antibody (Sigma) was deposited as a line in the control region (C) of the membrane using a Biodot dispenser at a predetermined concentration. A nicarbazin analogue was applied as a line in the target region (T) and the membrane then further processed by established methods. The internal control latex was mixed with nicarbazin specific latex and applied to the release region of the device by air jet. The processed strips were assembled onto cards, cut to dipsticks and then plastic housings.

Samples were prepared either by dilution of nicarbazin standard in a 10% methanol extraction buffer, or avian meal samples processed following a simple extraction method. 10 ml of absolute methanol added to 10 g meal, crushed thoroughly before the solvent portion removed and diluted ⅒ in extraction buffer.

Each test was analysed by the addition of 75 μl of sample to a LFD. Each individual test was allowed to run for 10 minutes and the reflectance measured using a portable LFD reader (Otsuka). Reflectance values were obtained for the reference area (R), the control line (C) and the target line (T). Values were also obtained for 20 minutes and 30 minutes post sample application.

The graph of FIG. 10 shows control (R–C) and target (R–T) reflectance units for two sample concentrations (0 ppm and 2 ppm nicarbazin) at 10, 20 and 30 minutes post sample application. It can be seen at 10 minutes that regardless of nicarbazin concentration the control line reflectance (R–C) remains constant, however the target line reflectance value (R–T) is reduced from 21 at 0 ppm to 12 at 2 ppm nicarbazin concentration. This trend is maintained at 20 minutes and 30 minutes however reflectance values are shown to increase slightly as the sample run time increases.

The second graph, shown in FIG. 11, shows the % inhibition of target line in relation to the control, calculated as $100-((R-T/R-C) \times 100)$, against time post sample application. The value obtained for zero nicarbazin remains approximately constant over the time course and similarly for the 2 ppm sample. The trend is maintained at 20 and 30 minutes.

These results show that the control reflectance is approximately constant irrespective of time post sample application or the presence of nicarbazin.

It is also demonstrated that there is a relationship between the concentration of nicarbazin within a sample and inhibition of target line development. Therefore an unknown sample could be semi-quantified based on the resultant level of inhibition, the greater the inhibition the higher the concentration of nicarbazin present within the sample.

EXAMPLE 7

Cortisol Detection

Cortisol is one of the most important marker hormones that are linked to the stress response in animals. Many methods for assessing stress levels, and consequently animal welfare, exist but tend to invasive and laborious. Measurement of salivary cortisol in domestic animals has been shown to have a direct correlation with levels of stress and as such forms the basis of a semi-quantitative LFD as a tool for monitoring animal welfare. A cortisol specific mouse monoclonal antibody and a BSA-cortisol conjugate were used to develop a competitive LFD. An internal control system was incorporated to produce a semi-quantitative assay. Sheep sera latex and an anti-sheep control line were employed, as described in Example 2.

A housed lateral flow device was assembled following normal best practices. The internal control was developed using a 0.4 µm blue latex particle, passively coated with negative sheep sera (Sigma), at 2 mg/ml concentration, following established methods. Anti sheep polyclonal antibody was deposited as a line in the control region (C) of the membrane using a Biodot dispenser at a predetermined concentration. A BSA-cortisol conjugate was applied as a line in the target region (T), the membrane then further processed by established methods. The internal control latex was mixed with cortisol specific latex and applied to the release region of the device by air jet. The processed strips were assembled onto cards, cut into dipsticks and then into plastic housings.

Samples were prepared either by dilution of hydrocortisone (cortisol) hemisuccinate salt standard in extraction buffer, or non-invasive collection of saliva from a test animal (pig). Each individual device was analysed by the addition of 75 µl of sample and allowed to run for 8 minutes. Reflectance was then measured using a portable LFD reader (Otsuka) and values obtained for reference area (R), the control line (C) and target line (T).

Both individual reflectance units for C and T, and % inhibition of T in relation to C are displayed in the graph (FIG. 12) for a range of standards in buffer (0, 1 and 12 ppb). It is shown that irrespective of cortisol concentration the control line reflectance (R−C) remains constant, however the target line reflectance (R−T) decreases from 21, approximately equal to the control line at zero concentration to <15 at 12 ppm cortisol concentration. This is shown as an approximate 28% inhibition of target line in relation to control where percentage inhibition is determined as 100−((R−T/R−C)×100)).

It has been demonstrated that there is a relationship between the concentration of cortisol within a sample and inhibition of target line development. Therefore an unknown sample could be semi quantified based on the resultant level of inhibition, the greater the inhibition the higher the concentration of cortisol present within the sample.

The invention claimed is:

1. A method for the determination of a target analyte in a sample, said method comprising:
    a) applying a liquid sample suspected of containing said target analyte to a solid support capable of allowing lateral flow of liquid therethrough, which support has diffusibly arranged thereon, (i) either (a) a labelled binding partner for said analyte or (b) a labelled analogue of said analyte, and (ii) a labelled control reagent;
    b) allowing the sample, labelled binding partner for said analyte or a labelled analogue of said analyte and labelled control reagent to flow through a detection zone on said solid support, wherein in the case of (i)(a) above, a predetermined amount of an analogue of the target analyte is immobilised, or, in the case of (i)(b) above a predetermined amount of a binding partner for said analyte or labelled analogue is immobilised;
    c) allowing the sample, labelled binding partner for said analyte or a labelled analogue of said analyte and labelled control reagent to flow through a control zone on said solid support which is spaced from said detection zone, and in which a binding agent which binds the labelled control reagent is immobilised, said binding agent being present in an amount sufficient to give a similar signal to that which occurs in the detection zone when it is fully occupied by either the labelled binding partner for said analyte or the labelled analogue of said analyte, and
    d) detecting the label density in the detection zone (T), and the label density in the control zone (C) and comparing these densities.

2. The method of claim 1, wherein the label density in a reference zone (R) on said solid support which is spaced from said control zone and from said detection zone, and in which no binding partners are immobilised, and the ratio of the difference between the label density in the reference zone (R) and the detection zone (T) to the difference between the label density in the reference zone (R) and control zone (C) is calculated to allow the amount of target analyte present in the sample to be determined in a semi-quantitative manner.

3. The method of claim 2, wherein the reference zone is approximately equidistant between the detection zone and the control zone on said solid support.

4. The method of claim 1, wherein the label densities are measured automatically using a signal reading device.

5. The method of claim 4, wherein the reading device further comprises a data processing device, which allows the results to be interpreted automatically.

6. The method of claim 1, wherein the labelled binding partner for the analyte or the labelled analogue of said analyte, and the labelled control reagent comprise a visible label.

7. The method of claim 6, wherein the visible labels are particulate labels.

8. The method of claim 7, wherein the labels are selected from the group consisting of latex, gold, and silica.

9. The method of claim 6, wherein the label densities are measured using a reflectance detector.

10. The method of claim 1, wherein the same label is used for the analyte specific binding partner or the labelled analogue of the analyte, and the labelled control reagent.

11. The method of claim 1, wherein the detection zone contains an analogue of the analyte immobilised thereon, and a labelled binding partner for the analyte is the diffusibly bound partner therefore.

12. The method of claim 11, wherein the analyte is a fungal protein and the analogue of the target analyte used as the immobilised element in the detection zone is a hormone or a fungal extract containing the target analyte.

13. The method of claim 11, wherein the analyte is a chemical reagent and the analogue of the target analyte is a protein-hapten conjugate where the hapten is the analyte or a derivative of the analyte.

14. The method of claim 1, wherein a known volume of sample is added to the solid support.

15. The method of claim 1, wherein the solid support contains a further diffusible labelled binding partner for a different analyte, a further detection zone each containing an immobilised analogue of said different analyte, or a binding partner for a different analyte, and the method is used to detect the presence of more than one analyte in a sample, and optionally a further diffusible labelled control reagent and a further control zone which is spaced from said further detection zone, and in which a further binding agent which binds the further labelled control reagent is immobilised, said further binding agent being present in an amount sufficient to give a similar signal to that which occurs in the further detection zone when it is fully occupied by either the labelled binding partner for said analyte or the labelled analogue of said analyte.

16. The method of claim 1, wherein the target analyte is selected from the group consisting of an agrochemical, a pesticide residue, a diagnostic marker protein, a hormone, a drug, and a drug residue.

17. The method of claim 16 wherein the target analyte is an active agrochemical contained within plant tissue, wherein said method comprises, in a preliminary step, extracting said plant tissue into a solvent in which said active agrochemical is soluble, and detecting active agrochemical within said sample.

18. The method of claim 17, wherein the results are used to determine whether further application of said agrochemical is required in order for the plant to benefit from the effect thereof.

19. The method of claim 17, wherein the plant tissue is leaf tissue.

20. The method of claim 19, wherein the leaf tissue is first subjected to a washing step so as to remove agrochemical from the surface thereof so that only agrochemical which has penetrated the leaf is detected.

21. The method of claim 17, wherein the plant tissue is root tissue.

22. The method of claim 1, wherein the target analyte is a hormone.

23. The method of claim 22, wherein the hormone is selected from the group consisting of progesterone, and cortisol.

* * * * *